United States Patent [19]

Baillie et al.

[11] 4,420,966

[45] Dec. 20, 1983

[54] METHOD FOR DETERMINING SOLIDS OR LIQUIDS IN VAPOR

[75] Inventors: Lloyd A. Baillie, Homewood; George A. Uhl, Crete, both of Ill.

[73] Assignee: Atlantic Richfield Company, Philadelphia, Pa.

[21] Appl. No.: 399,941

[22] Filed: Jul. 20, 1982

Related U.S. Application Data

[62] Division of Ser. No. 255,915, Apr. 20, 1981, abandoned, which is a division of Ser. No. 99,348, Dec. 3, 1979, Pat. No. 4,299,116.

[51] Int. Cl.³ .......................................... G01N 15/06
[52] U.S. Cl. ...................................................... 73/28
[58] Field of Search ............................................ 73/28

[56] References Cited

U.S. PATENT DOCUMENTS

2,684,008  7/1954  Vonnegut .......................... 73/28 X

Primary Examiner—James J. Gill
Assistant Examiner—Joseph W. Roskos
Attorney, Agent, or Firm—Stanley M. Welsh

[57] ABSTRACT

A method for measuring changes in the amount of solids or liquids entrained in vapor in a container includes introducing a first vapor purge stream into a first sensor, introducing a second vapor purge stream into a second sensor located at a different level from the first sensor, and measuring the relative pressure between the sensors as indicative of changes in the amount of entrained solids or liquids.

1 Claim, 8 Drawing Figures

METHOD FOR DETERMINING SOLIDS OR LIQUIDS IN VAPOR

This is a division of U.S. Ser. No. 255,915 filed Apr. 20, 1981, now abandoned, which is in turn a division of U.S. Ser. No. 099,348 filed Dec. 3, 1979, now issued as U.S. Pat. No. 4,299,116 (1981).

BACKGROUND OF THE INVENTION

1. Field of the Invention

This invention relates to methods for making relative pressure measurements by means of manometer-like devices. More specifically, this invention relates to methods for measuring the density of a vapor, changes in a liquid level, the average specific gravity of a liquid, changes in the amount of solids or liquids entrained in a vapor, and the interface between two immiscible liquids by means of manometer-like devices.

2. Prior Art

Methods for measuring relative vapor pressures, by means of manometer-like devices are well known. "Manometer-like" devices means throughout this specification and the claims a relative pressure measuring device wherein a first pressure is measured relative to a second pressure by balancing the difference in pressure between said first and second pressure by a fluid-head. A "fluid-head" means, throughout this specification and claims, the product of the difference in relative heights between a first fluid level, e.g., a first liquid and a second fluid level, e.g., a second liquid, times the density of said first and said second fluid, when said first and said second fluids are of the same density. More generally, a fluid-head, where two immiscible fluids, e.g., liquids, make up the "fluid-head" requires a balancing of the contributions made by each of the fluids, as is clear to one of skill in the art.

To determine vapor density by means of relative pressure measurements can involve very small changes in relative liquid levels. For example, changes in relative liquid levels can be less than one-thousandth of an inch. Similarly, to locate a a liquid interface by means of manometer-like devices may be very difficult since the changes in relative liquid levels can be very small, e.g., less than a thousandth of an inch.

BRIEF DESCRIPTION OF THE INVENTION

It is an object of this invention to provide an improved method for making determinations of the density of a vapor, the change in a liquid level, the average specific gravity of a liquid, changes in the amount of solids or liquids entrained in a vapor and the interface between two immiscible liquids by means of a manometer-like device.

Other objects of this invention will be clear to one of skill in the art based upon this specification.

It has been found that a photocell manometer-like device, as described below, is particularly suited for carrying out the above objects. A photocell manometer-like device comprises a reservoir, a measuring cell, a first liquid in the reservoir, a second liquid in the measuring cell, a transferring means for trasferring at least a portion of the first liquid and the second liquid, a first means for sensing a first pressure and a second means for sensing a second pressure, a detector means which produces a response signal which varies depending upon a signal interacting therewith, and a signal source for producing such a signal. The reservoir is connected to the measuring cell by the transferring means. The first liquid and the second liquid contained in the reservoir and the measuring cell, respectively, can flow between the reservoir and the measuring cell through the transferring means. The first means is connected to the reservoir so that the first pressure impinging upon the first means is transmitted in a substantially undiminished degree to a surface of the first liquid. The second means is attached to the measuring cell, so that a second pressure impinging on the second means is transmitted in a substantially undiminished degree to a surface of the second liquid. With the first device connected as hereinabove described, changes in relative value between the first pressure and the second pressure produces changes in an amount of the second liquid in the measuring cell. The signal source is located in a position relative to the second liquid so that a characteristic of a signal from the signal source is modulated or modified to produce a modulated signal. The characteristic varies with the amount of the second liquid. The detector responds to the characteristic of the modulated signal by producing a response signal. The response signal changes in an amount related to changes in the characteristic of the signal. A means for measuring is used to convert the response signal into an observable quantity or measurement. For example, a characteristic of a light signal is intensity. This intensity will vary depending upon the amount of the second liquid in the measuring cell when such light is transmitted through a thickness of the second liquid in the measuring cell where the thickness varies as the amount of liquid in the measuring cell varies. The amount by which the intensity of the signal varies with the thickness or width is discussed in more detail in an example.

The detector produces a response signal in response to a modulated signal. The response signal varies by an amount related to the amount that the characteristic of the signal is changed. An example of a response signal is voltage directly proportional to the resistance of a photoresistant material, such as cadmium sulfide. The resistance of cadmium sulfide varies depending upon the intensity of light impinging thereon.

The signal provided by the signal source of this invention must have a characteristic (1) which is modulated by the second liquid by an amount which depends upon the quantity of the second liquid in the measuring cell and (2) which induces a particular response signal from a detector. The particular response signal must be related to the amount by which the characteristic of the signal was modulated by the second liquid. A preferred way to modulate a signal is in relation to the intensity of the signal. Selected liquids having an appropriate k value defined in relation to Beer's Law are particularly advantageous in this invention. The density of such liquids can vary over a wide range of values. However, the less dense the liquid, all other factors being equal, the greater the amount of such liquid transferred between the measuring cell and the reservoir in response to a fixed pressure differential between the first and second means. Examples of such liquids suitable for use in this invention are water, alcohols, ethers and the like. Preferably, such liquids will have a sufficiently low vapor pressure so as not to volatilize rapidly or to any great extent. For example, liquids having a density in grams/cubic centimeter in the range of about 0.6 to about 2 can be used, provided they have a vapor pressure in the range of about 0 to about 5 grams/square centimeter at about 72° F. Liquids containing a dye or signal absorber are particularly advantageous. A liquid having a k value defined in relation to Beer's Law in the range of about 0.1 to about 1000 can be used. However, all other factors being equal, the lower the k value the lower the amount of modulation and hence the lower the sensitivity as discussed in an example. However, if the k value becomes too large, all other factors being equal, the amount of modulated signal which will reach the detector becomes too small to be easily measured or detected and problems from vibrations begin to occur. Preferably, the k value in reciprocal centimeters ($cm^{-1}$) is in the range of about 10 to 500, and still more preferably is in the range of about 50 to about 200.

Depending upon either the signal used, or the dye or signal absorber used, the k value in Beer's Law can be frequency dependent. To avoid a complicated Beer's Law dependence involving frequency, either the dye or signal absorber selected for use must have a k value which is substantially frequency independent, or the signal selected for use is limited to a range of frequencies wherein the k value of the dye or signal absorber is substantially constant. One way to limit the range of frequencies of the signal is by means of appropriate filters.

A means for measuring changes in the response signal of the detector is connected to the detector to permit such measurement. An example of a response signal is voltage or resistance converted into voltage. An example of a means for converting resistance into a voltage is a measuring circuit shown in FIG. 1.

The signal employed is electromagnetic radiation wherein the intensity, i.e., a characteristic of that radiation, is changed upon transmission through a layer of the second liquid in the measuring cell. The relationship between the intensity changes and liquid thicknesses is discussed in detail in an example. Preferably, the transmittance characteristics of a selected liquid will follow a simple form of Beer's Law, i.e., $I/I^0 = e^{-kH}$. The k is a constant which can be determined by a calibration procedure discussed in an example. Carbon black or graphite, e.g., in an india ink solution of about 1% has been found particularly suitable in this invention. The value of k in reciprocal centimeters is preferably in excess of about 50. More preferably, the value of k is in the range of in excess of about 50 to about 1000 reciprocal centimeters and most preferably in the range of about 50 to about 200 reciprocal centimeters.

One process of this invention involves a relative density determination of a vapor in a vertical zone having an inlet and an open outlet by means of a photocell manometer having a first sensor and a second sensor. This process comprises:

(1) continuously introducing the vapor into the inlet at a rate at least sufficient to maintain the zone completely filled with the vapor, and (2) measuring a pressure transmitted by the first sensor relative to a pressure transmitted by the second sensor, wherein the first sensor is connected to a lower portion of the zone and the second sensor is connected at a reference pressure. This process provides a method for continuously measuring and monitoring the relative density of the vapor.

Another process of this invention involves a determination of the density of a vapor in a vertical zone having an inlet at a bottom portion thereof, an outlet at the top portion thereof and circumferential walls by means of a photocell manometer having a first sensor and a second sensor. This process comprises:

(1) introducing through the inlet the vapor at a rate and for a time sufficient to completely and uniformly fill the vertical zone, (2) closing off the inlet, and (3) measuring a pressure transmitted by the first sensor relative to another pressure transmitted by the second sensor, wherein the first sensor is connected to a reference vapor at a reference pressure. The density of the vapor can then be determined relative to the reference vapor.

Another process of this invention involves measuring changes in a liquid level defined by a liquid-vapor interface within a container by means of a photocell manometer having a first sensor with an orifice and a second sensor. This process comprises:

(1) introducing a first purge stream at a rate and for a time sufficient to keep the liquid from entering into the orifice of the first sensor, wherein the orifice of the first sensor is below the liquid level, (2) introducing a second purge stream into the second sensor at a rate and for a time at least sufficient to keep the second sensor at a reference pressure, and (3) measuring a pressure transmitted by the first sensor relative to a pressure transmitted by the second sensor. Changes in the pressure transmitted by the first sensor relative to that transmitted by the second sensor can indicate a change in the liquid level.

Another process of this invention involves measuring the average specific gravity of a first liquid within a tank by means of a photocell manometer having a first and a second sensor. This process comprises:

(1) introducing a purge stream of a reference liquid into a hollow column having two open ends, a first and a second end, wherein the first end is above a surface level defined by the first liquid, and the second end terminates near a bottom of the tank at a distance space from the bottom at least sufficient to permit the reference liquid to exit from the second end, and wherein the rate of introducing the purge stream is at least sufficient to maintain the column which is within said first liquid uniformly and completely filled with the reference liquid, (2) introducing a first vapor purge stream into the first sensor which has an orifice thereof located below the surface level defined by the first liquid at a rate at least sufficient to keep the first liquid from entering the orifice of the first sensor, (3) introducing a second vapor purge into the second sensor which has an orifice thereof located within the reference liquid at a rate at least sufficient to keep the reference liquid from entering the orifice of the second sensor, wherein the orifices of the first and second sensors are at the same height relative to one antoher, and (4) measuring a difference in a pressure transmitted by the first sensor relative to a pressure transmitted by the second sensor.

This process provides a method for measuring the relative density of the first liquid as compared to the reference liquid based upon a difference in pressure determined in the above-described manner. Preferably, the rate at which the reference liquid is introduced into the column is just sufficient to maintain the column uniformly filled with the reference liquid. As the reference liquid difuses or exits from the second end, the density of the first liquid can be affected if the volume of the first liquid is too small and for this reason the rate of addition of the reference liquid should be kept as low as possible while maintaining the column uniformly filled with the reference liquid.

Another process of this invention involves measuring changes in the amount of solid or liquids entrained in a vapor contained in a vertical container, e.g., a distillation column, by means of a photocell manometer having a first sensor and a second sensor located at different levels within the container. This process comprises:

(1) introducing a first vapor purge stream into the first sensor at a rate at least sufficient to maintain the first sensor uniformly filled with a vapor from the first vapor purge stream, (2) introducing a second vapor purge stream into the second sensor at a rate at least sufficient to maintain the second sensor uniformly filled with a vapor from the second vapor purge stream, (3) locating an orifice of the first sensor at a different relative height to an orifice of the second sensor, and (4) measuring a pressure transmitted by the first sensor relative to a pressure transmitted by the second sensor. Differences in relative pressure determined as described above indicates changes in the amount of entrained solids or liquids.

Another process of this invention involves determining the location of an interface between a first and a second liquid that are immiscible with respect to one another by means of a photocell manometer having a first sensor and a second sensor. This process comprises:

(1) locating an orifice of the first sensor and an orifice of the second sensor at a fixed difference in relative height with respect to one another, wherein one orifice of the orifices of the first and the second sensor is within a region containing the first liquid and a second orifice of the orifices of the first and the second sensors is within a region containing the second liquid, (2) introducing a first vapor purge into the first sensor at a rate and for a time at least sufficient to keep liquid from entering into the orifice of the first sensor, (3) introducing a second vapor purge into the second sensor at a rate and for a time at least sufficient to keep liquid from entering into the orifice of the second sensor, and (4) measuring a pressure transmitted by the first sensor relative to a pressure transmitted by the second sensor. The pressure difference between the pressures transmitted by the first and the second sensors can be used to calculate the location of the interface between the first liquid and the second liquid, provided the density of the first liquid and the second liquid are known.

Another process of this invention involves the determination of the density of a liquid by means of a photocell manometer. The photocell manometer has a first sensor connected to a pressure compensation and transmission means. The pressure compensation and transmission means includes a pressure transfer means with a first orifice and a pressure compensation means. The photocell manometer also has a second sensor with a second orifice. The pressure compensation and transmission means can include two conduits wherein a compensation bubbler separates the two conduits. This process comprises:

(1) introducing a first vapor purge stream into the first sensor at a rate at least sufficient to maintain the first sensor and the pressure compensation and transfer means uniformly filled with a vapor from the first vapor purge stream, (2) introducing a second vapor purge stream into the second sensor at a rate at least sufficient to maintain the second sensor uniformly filled with a vapor from the second purge stream, (3) locating the first orifice and the second orifice within the liquid at a selected vertical height separation therebetween, (4) compensating at least a portion of any pressure differential impinging on the first orifice relative to the second orifice by means of the pressure compensator means, and (5) measuring a relative pressure transmitted by the first sensor relative to a pressure transmitted by the second sensor.

Figure 8:
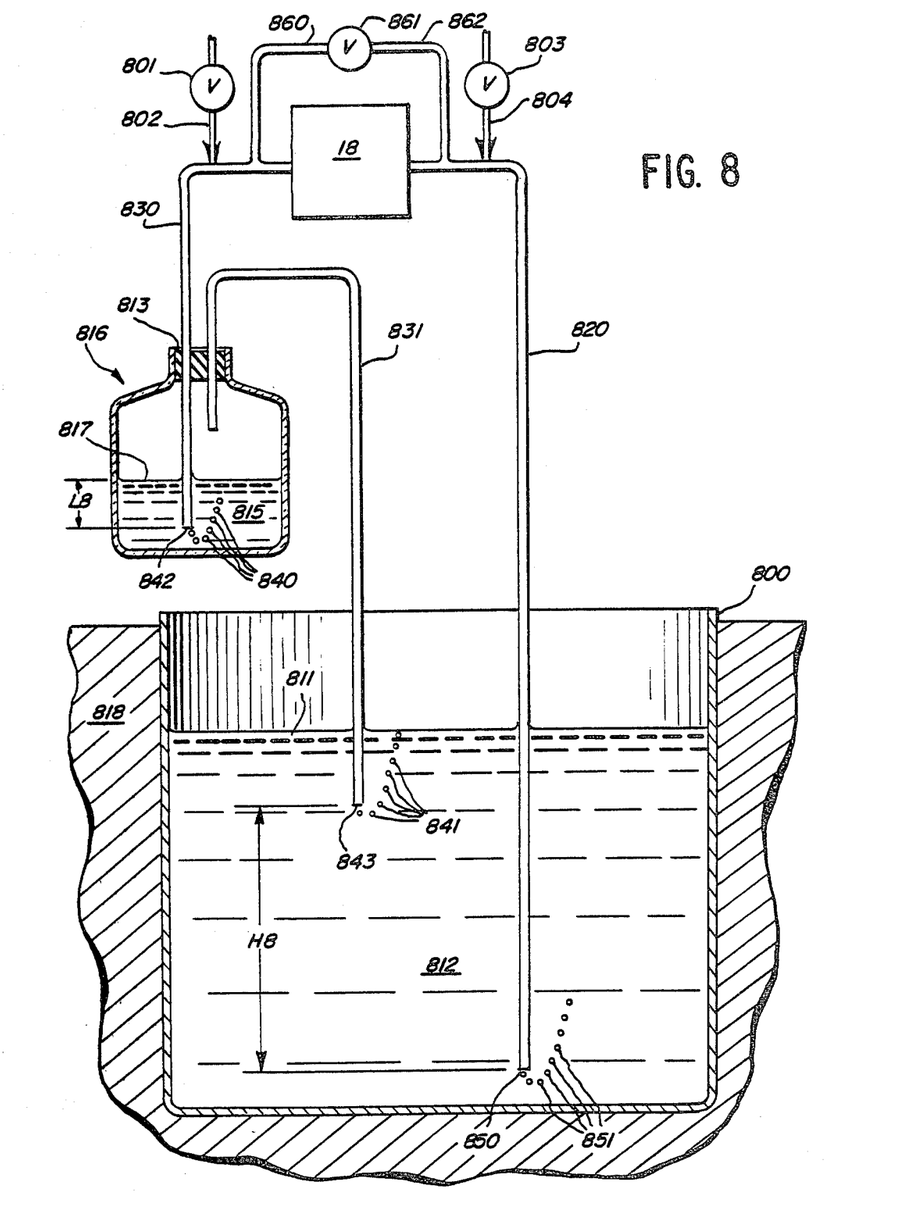
FIG. 8 discloses an apparatus for determining on a continuous basis, the average density of a liquid and/or changes in that average density.

With the process carried out in the above-described manner, the density of the liquid can be determined from the following relationship:

$$De = (Del(p) + Comp.(P))/H8$$

where
De is said density of said liquid,
Del(p) is the differential pressure measured by said photocell manometer,
Comp.(P) is the amount of pressure provided by compensating at least a portion of any pressure differential impinging on said first orifice relative to said second orifice, and
H8 is the selected vertical height separation between said first orifice and said second orifice as shown in FIG. 8.

DETAILED DESCRIPTION OF THE INVENTION

Figure 1:
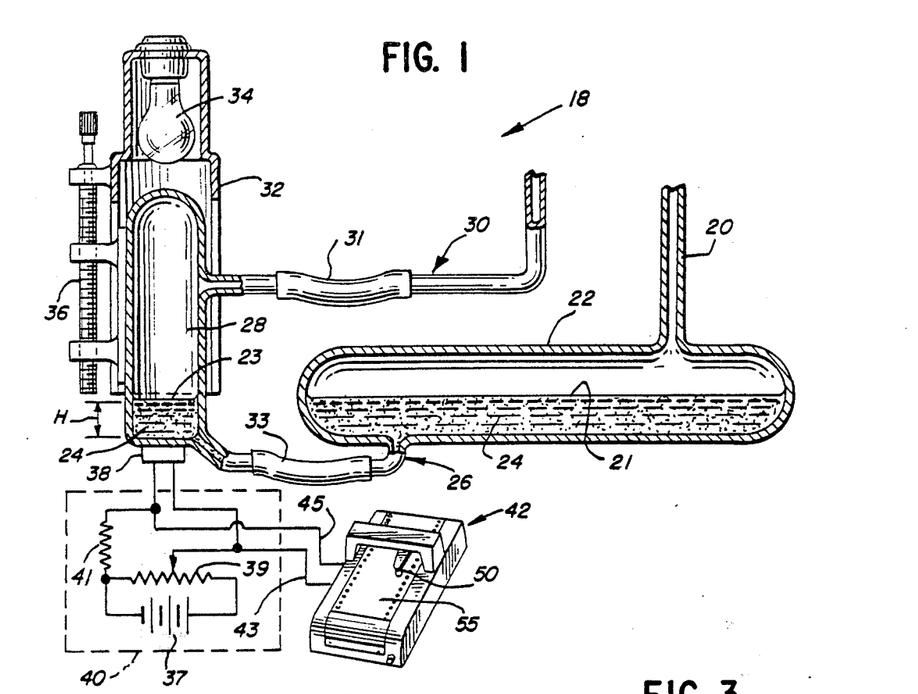
FIG. 1 discloses a photocell manometer useful in carrying out the processes and methods of this invention.

In FIG. 1, there is the photocell manometer 18 consisting of a first sensor or conduit 20, a reservoir 22, containing a liquid 24, a conduit or connection 26, a measuring cell 28, a second sensor or conduit 30, a support 32, a light or signal source 34, a threaded shaft or screw 36, a detector 38, a measuring circuit 40, and a millivolt recorder 42. Conduit 26 includes a flexible conduit portion 33, and conduit or second sensor 30 includes a flexible conduit portion 31 to permit some relative movement between measuring cell 28 and reservoir 22.

Support 32 supports both measuring cell 28 and signal source 34. Measuring cell 28 along with detector 38 can be moved very accurately relative to reservoir 22 by means of a threaded screw 36. A change in position of measuring cell 28 relative to reservoir 22, produces a change in H. As discussed in more detail in an example, the amount of light or signal transmitted through liquid 24 can be used to determine changes in H and hence pressure differences. Briefly, the operation of the photocell manometer 18 of FIG. 1 is described hereinafter.

The pressure transmitted by the first sensor or conduit 20 is transmitted preferably in substantially undiminished amount to surface 21 of liquid 24 in reservoir 22. The pressure transmitted by the second sensor or conduit 30 is transmitted preferably in a substantially undiminished amount to surface 23 of liquid 24 in measuring cell 28. The amount of liquid 24 transferred between reservoir 22 and measuring cell 28 will depend upon the difference in pressure on surfaces 21 and 23 and the relative size of the areas defined by surfaces 21 and 23. All other factors being equal, the greater the pressure difference, the more liquid 24 that will be transferred. The amount of liquid 24 transferred is directly related to differences in H shown in FIG. 1.

Measuring cell 28 can be moved very accurately to different heights or levels relative to reservoir 22 by means of threaded shaft 36. A signal source 34 (powered by a source not shown) transmits electromagnetic radiation, e.g., light radiation, through liquid 24 to detector 38.

Measuring circuit 40, consisting of a constant voltage source or battery 37 and resistors 39 and 41, is connected across detector 38. Variable resistor 39 permits a controlled amount of voltage to be drawn from battery 37 and imposed across resistor 41 and detector 38. Resistor 41 and detector 38 are in series with one another. The voltage differences across detector 38 is measured and recorded by means of millivolt recorder 42. Battery 37, for example, can have a voltage of 1.5 volts when resistor 39 has a variable resistance of from 0 to 1,000 ohms and resistor 41 has a resistance of about 100,000 ohms. Detector 38 preferably uses cadmium sulfide.

Figure 2:
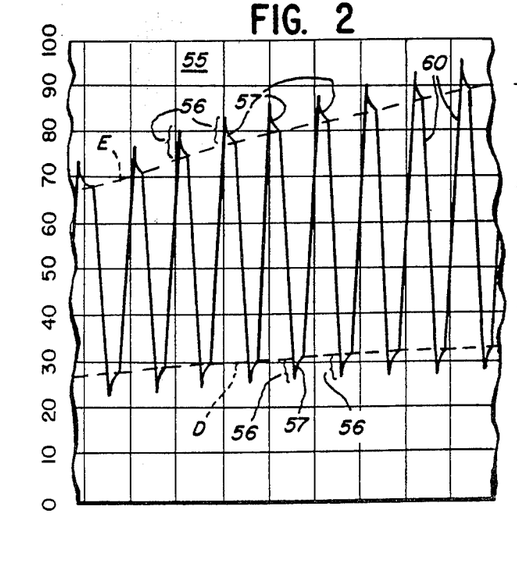
FIG. 2 discloses an enlarged portion of a strip chart such as would be produced by the microvolt recorder of FIG. 1.

Measuring circuit 40, shown schematically, converts the resistance across detector 38 into a voltage differential across detector 38. This voltage differential across detector 38 is measured and recorded by millivolt recorder 42 on a strip chart 55. FIG. 2 is an enlarged view of a strip chart 55 from millivolt recorder 42.

The apparent resistance across detector 38 will vary depending upon the intensity of light radiation impinging thereon. The amount of transmitted light radiation reaching detector 38 from light source 34 will vary, all other factors to be discussed hereinafter being equal, logarithmically with the height H of liquid 24.

In a preferred embodiment, the transmittance characteristics of liquid 24 will follow a simple form of Beer's Law, i.e. $I/I_0 = e^{-kH}$. The k is a constant which can be determined by a calibration procedure discussed in an example. Carbon black or graphite e.g., in an india ink solution of about one percent (1%) has been found particularly suitable in this invention. The value of k in reciprocal centimeters is preferably in excess of 50. The larger the value of k, the more sensitive is the instrument. If k becomes too large, e.g., much above 1000, minute vibrations can become a serious problem and/or the intensity of transmitted light can become diminished to a point that makes detection difficult. Preferably, k has a value in the range of about 50 to about 200 reciprocal centimeters.

Variables in photocell manometer 18 that can both affect millivolt recorder readings and be avoided by an automatic self-calibration, to be described in more detail hereinafter with respect to FIG. 2, are: (1) variations in light or signal intensity from light or signal source 34, (2) variations in voltage of battery 37, (3) changes in temperature of liquid 24, and (4) mechanical stresses which slowly change the configuration of the photocell manometer system. Changes in light intensity from signal source 34 can arise, for example, in two (2) ways. The first way is the result of aging of the bulb of signal source 34 and the second way is due to variations in line voltage from a power source not shown to the bulb of light source 34. Variations in voltage of battery 37 can occur over time as energy is continuously being drawn from battery 37. Mechanical stresses can, for example, change the dimensions of flexible conduit portion 33, reservoir 22 or measuring cell 28. Such changes due to mechanical stresses are expected to be insignificant. By "slowly" is meant slow in comparison to the duration of a calibration cycle. A calibration cycle is discussed with respect to FIG. 2.

FIG. 2 represents a strip chart 55 from millivolt recorder 42. A recording pen 50 moves an amount linearity proportional to the potential difference due to input of leads 43 and 45. The strip chart itself is driven at a suitable speed to provide a time component to transverse movement of recording pen 50. When there is no voltage difference between input leads 43 and 45, pen 50 is zeroed to read 0 on the strip chart. In the operation of this invention, pen 50 will usually register something other than 0 because detector 38 will usually have some potential difference across itself when operating properly. When the pressure difference on surfaces 21 and 23 are equal, base line D is the value recorded by pen 50 due to a potential difference across detector 38. Top line E is the value recorded, when there is some pressure difference between surfaces 21 and 23. Such pressure differences cause a change in height H of FIG. 1, which in turn changes the intensity of light impinging on detector 38. Changes in light intensity impinging on detector 38 result in changes in a measurable characteristic, e.g. the internal resistance, of detector 38. Changes in the internal resistance of detector 38 result in changes in voltage drop measured across detector 38. These voltage drops across detector 38 are preferably linearly proportional to changes in the intensity of light impinging upon detector 38. The changes in intensity of light impinging upon detector 38 are in turn logarithmically related to changes in the height H of liquid 24.

The pen 50 produces a continuous line on strip chart 55. Depending upon how sensitive the gain for the null conduit is set, as is well known to a person of skill in the art, this line can consist of a substantially linear portion 60 having an over-shoot portion 56 and a non-linear asymptotic portion 57. Millivolt recorder 42 moves the pen by means of a null circuit commonly known in the art. The pen moves until a null point is reached. Because of the momentum of pen 50, the null point can be exceeded by an over-shoot portion 56. Pen 50 then asymptotically reaches the true null point along curved line 57. The true readings for the actual voltage drop across detector 38 are defined by dotted lines D and E which tangentially intersect the most linear end portion of asymptotic or curved lines 57.

As derived in the example, the ratio of $V_d$, the value in volts of base line D, to $V_e$, the value in volts of top line E, is very close to the value of the ratio of $R_0$, the internal resistance across detector 38 when the pressure on surfaces 21 and 23 are equal, to R, the internal resistance of detector 38 when there is some pressure difference impinging on surfaces 21 and 23, provided $V_w$, the total voltage dropped across detector 38 and resistor 41 is much larger than the voltage drop across detector 38, i.e. $V_d/V_e$ substantially equals $R_0/R$, provided $V_w$ is much larger than the individual voltage values $V_d$ and $V_e$.

A calibration cycle includes at least one measurement, e.g. Vd, wherein the pressures on surfaces 21 and 23 have been equalized, and at least one measurement, e.g. Ve, wherein the pressure on surfaces 21 and 23 are unequal.

Figure 3:
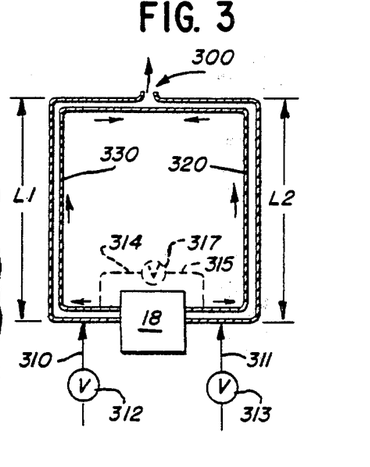
FIG. 3 discloses an apparatus for measuring the density of a vapor.

In FIG. 3, the apparatus disclosed for measuring the density of a vapor comprises: a photocell manometer 18, a vent 300, conduits 310, 311, 314, 315, 320 and 330, and valves 312, 313, and 317. Photocell 18 is shown schematically as a box. It functions in the same manner as discussed in FIG. 1. The first and second sensors are shown at opposite ends of the box for convenience. Conduit or first sensor 320 preferably corresponds to a different form of the first sensor 20 of FIG. 1, but can alternatively correspond to a different form of second sensor 30 of FIG. 1. Similarly, conduit or second sensor 330 preferably corresponds to a different form of the second sensor 30 of FIG. 1, but can alternatively correspond to a different form of first sensor 20 of FIG. 1. Both conduits 320 and 330 function in the same manner as corresponding conduits 20 and 30 to transfer pressure within each such conduit to surfaces 21 and 23, respectively, of liquid 24 of FIG. 1.

The operation of the apparatus in FIG. 3 is discussed hereinafter. A reference purge is introduced into conduit 310 which contains a valve 312. With valve 312 open, vapor of the reference purge enters conduit 330 from conduit 310 and exits through vent 300. Similarly, with valve 313 open, vapor of a sample purge, whose vapor density is to be determined relative to the vapor of the reference purge, enters conduit 320 (from conduit 311 and exits through vent 300. The reference purge and the sample purge are each located so vapor from each purge completely fills conduit 330 and conduit 320, respectively, i.e., the conduit through which it is made to flow. In other words, a column of height L1 of reference vapor will completely fill conduit 300 and a column height of L2 of sample vapor will completely fill conduit 320. L1 is equal to L2 and therefore any pressure differential measured by photocell manometer 18 will relate directly to the difference in density of the reference vapor relative to the sample vapor as discussed in more detail in EXAMPLE 2.

Optionally, conduit 314 and 315 having a valve 317 therebetween may be used so as to make equal the pressure on surfaces 21 and 23 of FIG. 1. If valve 317 is open and vapor is permitted to flow from first sensor 320 to second sensor 330 and vice versa until equilibrium is established, then the pressure on the liquid surfaces 21 and 23 of photocell manometer 18 will be equal.

Vent 300 insures that pressure on the vapor of the reference purge and the vapor of the sample purge will be equal.

Figures 4, 6:
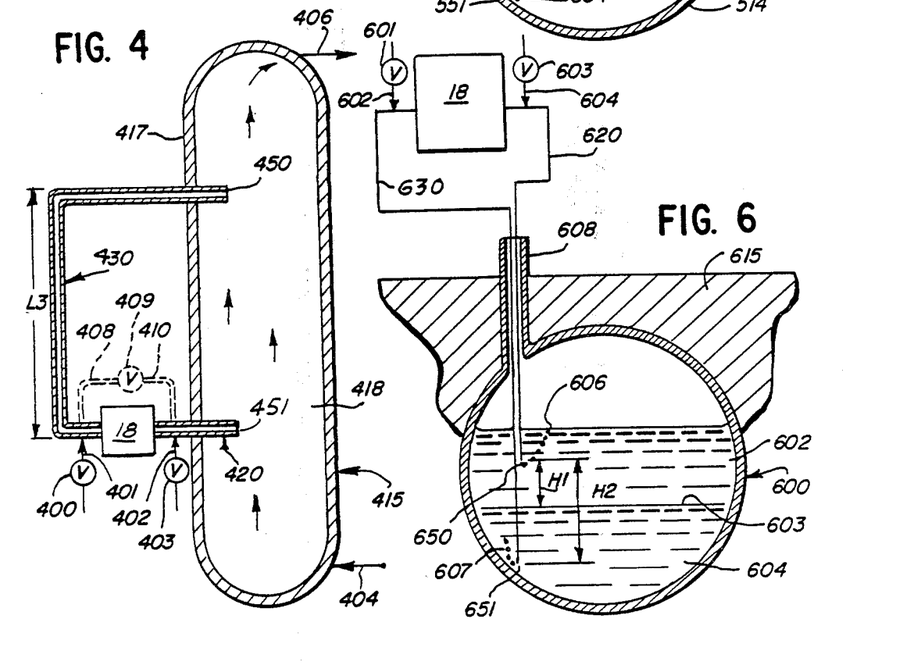
FIG. 4 discloses an apparatus for measuring the amount of entrained liquid or solid in a vapor.
FIG. 6 discloses an apparatus for determining a liquid interface between the two immiscible liquids.

In FIG. 4, there is shown a photocell manometer 18, conduits 401, 402, 404, 406, 408, 410, 420 and 430, valves 400, 403, and 409. Conduits 420 and 430 are preferably different forms, respectively, of conduits 20 and 30 shown in FIG. 1, but can alternatively correspond to different forms, respectively, of conduits 30 and 20 shown in FIG. 1. Conduits 420 and 430 function in the same manner to transfer pressure as corresponding conduits 20 and 30. Conduits 420 and 430 extend through wall 417 of distillation column 415 into vapor 418. L3 is the difference in relative height between orifice 450 of conduit or second sensor 430 and orifice 451 of conduit or first sensor 420. With corresponding valves 400 and 403 open, vapor of purge gases are transferred through conduits 401 and 403, respectively, into conduits 430 and 420, respectively. The location of each purge is selected to insure that the conduits 420 and 430 are uniformly filled with vapor. Distillation column 415 has an inlet conduit 404 and an outlet conduit 406. Distillation column 415 is shown schematically with arrows, to indicate the flow of vapors moving from conduit 404 to outlet conduit 406. It is not uncommon in a distillation column for vapor 418 to contain entrained liquids. These liquids can have an adverse affect on the overall efficiency of the distillation column.

Discussed hereinafter is a brief description of how photocell manometer 18 determines the changes in amounts of entrained solids or liquids in vapor 418 contained in distillation column 415. The relative pressure differential measured by photocell manometer 18 in the configuration disclosed in FIG. 4 reveals the difference in apparent vapor density of the purge vapor in conduit 430 versus a column of equal height of vapor 418 impinging an orifice 451 of conduit 420. Changes in the relative density of vapor 418 as compared to purge vapor in conduit 430 is a function of the amount of entrained solids or liquids present in vapor 418 as discussed in more detail in EXAMPLE 6.

Figure 5:
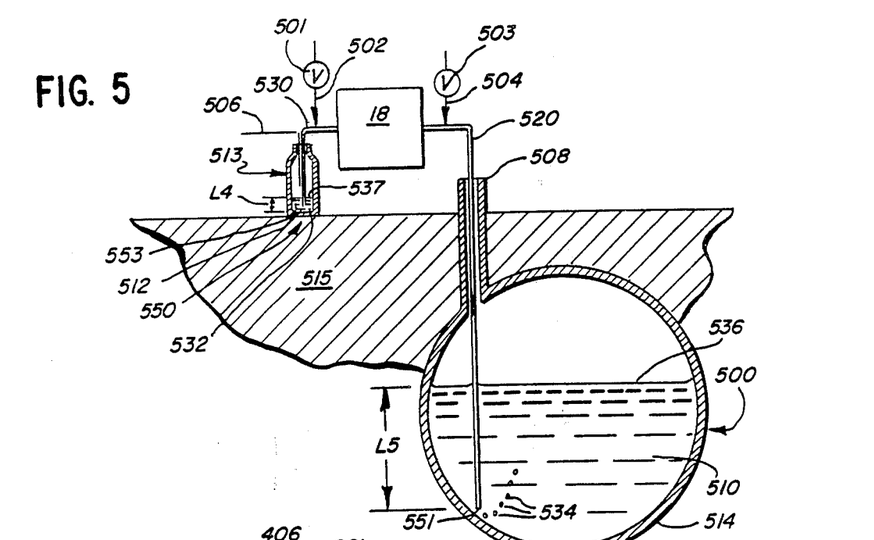
FIG. 5 discloses an apparatus for measuring changes in the level of a liquid contained in a storage tank so as to be able to determine whether there are any leaks.

FIG. 5 discloses an apparatus for measuring changes in the level of a liquid contained in a storage tank so as to be able to determine whether there are any leaks. The main components disclosed in FIG. 5 are: a photocell manometer 18, a reference bubbler 413, a storage tank 500, and two vapor purge conduits 502 and 504. As in other figures, photocell manometer 18 is shown schematically with first and second sensors 520 and 530 on opposite sides. First and second sensors 520 and 530 are preferably different forms of first and second sensors 20 and 30, respectively, of FIG. 1, but can correspond to different forms of second and first sensors 30 and 20, respectively, of FIG. 1 and function in the same manner to transfer pressure to surfaces 21 and 23 of liquid 24 of FIG. 1.

Storage tank 500, which is in ground 515 and contains stored liquid 510, can have dimensions as large as, for example, 6 feet in diameter by 10 feet in length. Fill pipe 508 provides an above ground opening which leads to the interior of storage tank 500 through a wall 514.

First sensor or conduit 520 extends through fill pipe 508 into the interior of storage tank 500 and below surface 536 of stored liquid 510. Orifice 551 at the end of first sensor or conduit 520 is always spaced from the bottom of storage tank 500 by an amount at least sufficient to permit purge vapor 534 to escape from the interior of conduit 520. A positive pressure of purge 534 is maintained within first sensor or conduit 520. Purge vapor 534 is introduced into conduit 520 through conduit 504 with valve 503 open. The flow rate of purge vapor 534 is preferably in the range of about 2 cm/minute to 20 cm/minute. The purpose of the purge vapor 534 is to maintain conduit 520 filled with purge vapor. Purge vapor at a pressure greater than the pressure, which is due to stored liquid 510, on orifice 551 exits through orifice 551. In FIG. 5, the exit of purge vapor is indicated by bubbles 534.

Second sensor or conduit 530 extends into reference bubbler 513 and below surface 537 of reference liquid 512. A second purge vapor is introduced through conduit 502 with valve 501 open into conduit 530. The purpose of the second purge is to maintain conduit 530 completely filled with purge vapor. Purge vapor at a pressure greater than the pressure, which is due to reference liquid 512, on orifice 550 exits orifice 550 in the form of purge vapor bubbles 553. Orifice 550 is spaced away from the bottom of reference bubbler 513 by a distance at least sufficient to permit second purge vapor to escape from orifice 550. The second purge vapor which has exited from orifice 550 eventually exits through outlet conduit 506.

The pressure impinging on orifice 551 by stored liquid 510, all other factors being equal, such as atmospheric pressure, will depend solely on the height L5. L5 is the distance between surface 536 and orifice 551. The pressure impinging on orifice 551, all other factors remaining equal, will depend on the product of the density of stored liquid 510 times L5. The pressure on orifice 550 by reference liquid 512, all other factors remaining equal, will depend upon the product of the height L4 times the density of reference liquid 512. L4 is the distance between the surface 537 of reference liquid 512 and orifice 550 of conduit 530.

The pressure on surface 21 of liquid 24 of photocell manometer 18 transmitted by first sensor 520 will be reduced by the vertical column of first purge vapor contained within conduit 520. The pressure impinging on orifice 551 will be equal to the product of the density of stored liquid 510 times height L5 plus the atmospheric pressure impinging on surface 536.

The pressure impinging on surface 23 of liquid 24 in photocell manometer 18 is transferred by second sensor or conduit 530 will be reduced by the vertical height of any first purge vapor contained in conduit 530. The pressure impinging on orifice 550 of second sensor or conduit 530 will be equal to the density of reference liquid 512 times height L4 plus the atmospheric pressure impinging on surface 537 of reference liquid 512.

Since the same atmospheric pressure will be impinging on surfaces 536 and 537, the difference in pressure measured by photocell manometer 18 will be unaffected by this portion of the pressure. Further, since the lengths of conduits 520 and 530 corresponding to a vertical height component are constant, the reduction in pressure as a result of purge vapor contained in conduit 520 and 530 will remain constant. Height L4 will remain constant. Therefore, any change in relative pressure measured by photocell manometer 18 will be due to a change in height L5 of stored liquid 510.

In practice, since very small changes in liquid levels within photocell manometer can be detected, the operation of the photocell manometer in FIG. 5, involves a zeroing of the effective pressures measured by photocell manometer 18 which are transferred by conduits 520 and 530, respectively. This is achieved by selecting a reference liquid 512 with an appropriate density and height L4. By varying height L4 of reference liquid 512, various pressures on orifice 550 of conduit 530 can be achieved. A conventional manometer-like device can be employed to balance the pressures transmitted by conduit 530 relative to conduit 520. Once a balance has been achieved between the pressure transmitted by conduit 530 versus the pressure transmitted by conduit 520, photocell manometer 18 is brought into the system as shown in FIG. 5. Changes in the surface level 536 of stored liquid 510 in storage tank 500 will change the height L5 and consequently change the pressure impinging on orifice 551. As discussed in more detail in EXAMPLE 3, measurements of relative vapor pressure can then be employed to indicate the presence of very small leaks, for example, on the order of 0.01 gallons.

FIG. 6 discloses an apparatus for determining a liquid interface between two immiscible liquids. Storage tank 600 contains two liquids, a first liquid 602 and a second liquid 604 which are immiscible with respect to one another, and therefore have an interface 603 therebetween. Storage tank 600 is, in this example, located in ground 615.

Photocell manometer 18 in FIG. 6 is shown schematically as in previous FIG. 5. First sensor or conduit 20 is preferably a different form of first sensor 20 of FIG. 1, but can be a different form of second sensor 30 of FIG. 1. Second sensor 630 is preferably a different form of second sensor or conduit 30 of FIG. 1, but can be a different form of first sensor 20 of FIG. 1. First sensor or conduit 620 and second sensor or conduit 630 transmit pressures to surfaces 21 and 23 of FIG. 1.

First sensor or conduit 620 extends through fill pipe 608 into the interior of storage tank 600 a sufficient distance so that orifice 650 is within first liquid 602. Second sensor or conduit 630 extends through fill pipe 608 into the interior of storage tank 600 so that orifice 651 is within second liquid 604. With orifice 650 of first sensor 620 within first liquid 602 and orifice 651 of second sensor 630 in second liquid 604, interface 603 is between orifice 650 and orifice 651. In this configuration, the difference in pressure, measured by photocell manometer 18, will permit one to calculate the location of interface 603 between orifice 650 and 651 as discussed in more detail in EXAMPLE 5. Optionally, to permit a greater range of values for the difference in pressure to be measured, a compensation bubbler, such as discussed in FIG. 8, e.g., compensation bubbler 816, can be added to first sensor 20.

Figure 7:
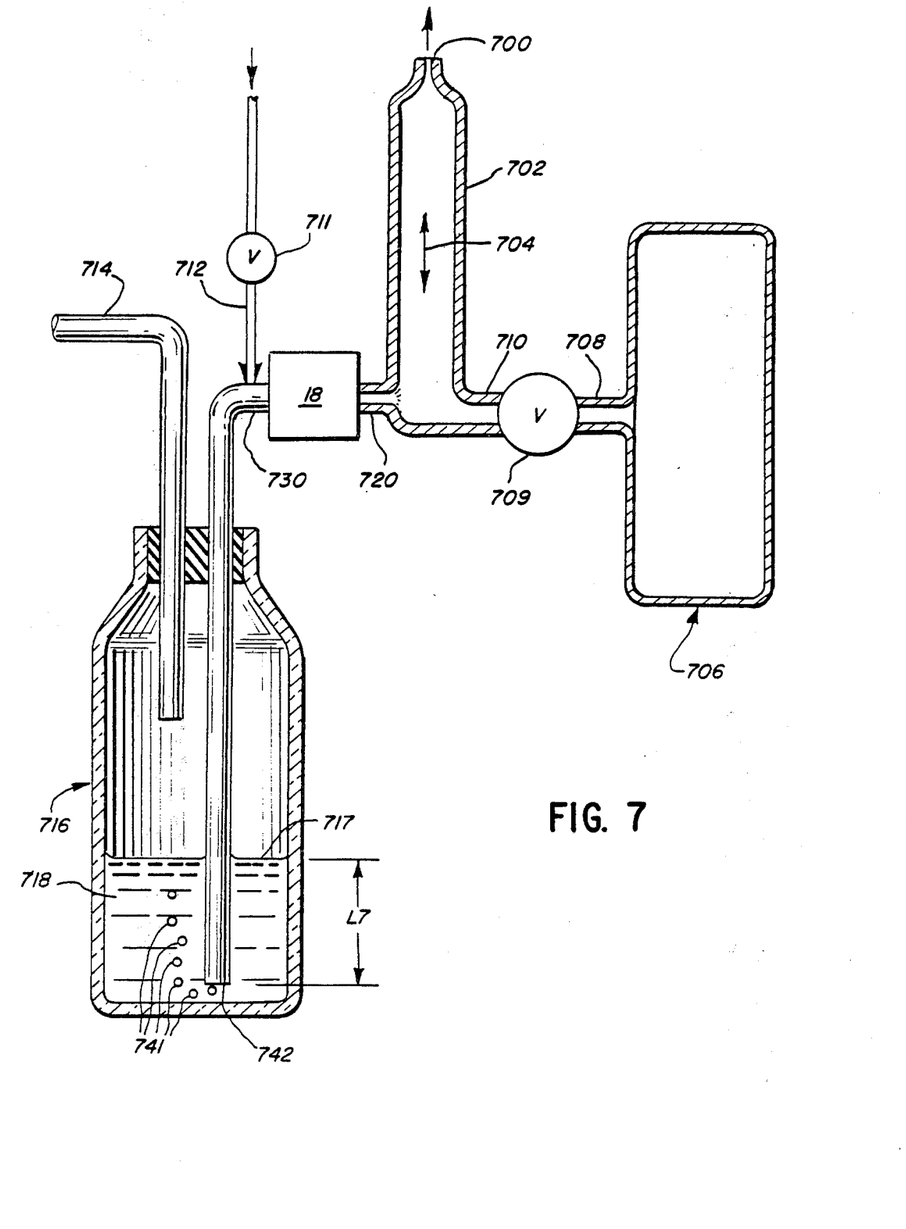
FIG. 7 discloses an apparatus for continuously monitoring the density of a vapor.

FIG. 7 discloses an apparatus for continuously monitoring the density of a vapor. The main components in FIG. 7 are: a photocell manometer 18, a column 702, conduits 708, 710, 712, 714, 720, and 730, valves 709 and 711, a vapor source 706 and a reference bubbler 716. As in other figures, photocell manometer 18 is shown schematically with first and second sensors 720 and 730 on opposite sides. The first and second sensors 720 and 730 are different forms of first and second sensors 20 and 30, respectively, of FIG. 1 or alternatively different forms of second and first sensors 30 and 20, respectively, of FIG. 1 and function in the same manner to transfer or transmit pressure within each conduit to surfaces 21 and 23 of liquid 24 of FIG. 1. Reference bubbler 716 contains a reference liquid 718.

A reference purge enters through conduit 712 with valve 711 open into second sensor or conduit 730. The vapor of the reference purge exits from orifice 742 of conduit 730 in the form of reference vapor bubbles 741. The reference purge vapor eventually exits reference bubbler 716 through outlet conduit 714.

Second sensor or conduit 730 extends into reference bubbler 716 and below the surface 714 of reference liquid 718. Orifice 742 of conduit 730 is spaced above the bottom of reference bubbler 716 so as to permit free escape of reference vapor bubbles 741.

Second sensor or conduit 720 is in vapor communication with the interior or vertical zone 704 of column 702. Vapor source 706 is connected to a lower portion of column 702 by means of conduits 708 and 710. Valve 709 permits the vapor passage between vapor source 706 and column 702 to be closed off. With valve 709 open, vapor from source 706 enters conduit 708 and 710 and eventually enters column 702. Vapor is permitted to enter column 702 from vapor source 706 in such a way as to completely fill vertical zone 704 with vapor of source 706. Excess vapor exits vertical zone 704 through vent 700. Vent 700 being open to the atmosphere insures that the pressure of vapor from source 706 does not vary depending upon the pressure under which the source vapor was stored.

To monitor the density of a vapor from source 706 continuously, the initial vapor pressure due to a column of vapor from source 706 in vertical zone 704 is first balanced against a reference bubbler 716 by suitably selecting a reference liquid 718 and adjusting the height L7 of that reference liquid 718. In FIG. 7, a rough balance between the vapor pressure of a vapor from source 706 in vertical zone 704 is established against reference liquid 718. The balance is achieved by adjusting height L7 to an appropriate level in much the same way as the reference bubbler 515 of FIG. 5. Various pressures on surface 23 of liquid 24 of FIG. 1 transmitted by second sensor or conduit 730 are achieved by varying either the density of reference liquid 718 and/or the distance L7. Distance L7 is the distance between orifice 742 of conduit 730 and surface 717 of reference liquid 718.

The apparatus of FIG. 7 operates as hereinafter described. First, a balance in terms of the pressure on surfaces 21 and 23 of liquid 24 of FIG. 1 is achieved by varying the density of reference liquid 718 and/or the distance L7. Any changes of the relative pressure on surfaces 21 and 23 will then be due to changes in the density of vapor from source 706, provided the vapor from reference purge entering through conduit 712 remains constant and the height L7 of reference liquid 718 remains constant. The atmospheric pressure impinging on surface 717 will be equal to the atmospheric pressure impinging on vapor exiting vent 700 and will therefore cancel one another. The apparatus of FIG. 7 permits two different types of measurements to be made. One type of measurement is an absolute determination of the relative vapor density of vapor from source 706. The other type of measurement is a determination of any changes in the density of a vapor from source 706 over a period of time. Clearly, any changes in the relative pressure sensed by sensors 730 and 720 with respect to one another will represent changes in the density of vapor from source 706.

FIG. 8 discloses an apparatus for determining on a continuing basis the average density of a liquid. Disclosed in FIG. 8 are a photocell manometer 18, conduits 802, 804, 820, 830, and 831, valves 801 and 803, a compensation bubbler 816 and a tank 800 in ground 818. As in other figures, photocell manometer 18 is shown schematically with first and second sensors 820 and 830 on opposite sides. First sensor or conduict 820 is preferably a different form of first sensor 20 of FIG. 1, but can be a different form of second sensor 30 of FIG. 1. Second sensor 830 is preferably a different form of second sensor or conduit 30 of FIG. 1, but can be a different form of first sensor 20 of FIG. 1. First sensor 820 and second sensor 830 each transmits a pressure to surfaces 21 and 23, respectively, of FIG. 1.

The first sensor 820 extends into liquid 812 stored in tank 800. Orifice 850 of conduit 820 is spaced from the bottom of tank 800 by a distance at least sufficient to permit free escape of purge buffers 851.

The second sensor 830 extends through stopper 813 into bubbler liquid 815. Orifice 842 of conduit 830 is spaced from the bottom of compensation bubbler 816 by a distance at least sufficient to permit the free escape of purge bubbles 840. Conduit 831 having one end spaced above surface 817 of bubbler liquid 815 extends through stopper 813 and into liquid 812. Orifice 843 of conduit 831 extends below surface 811 of liquid 812. Orifice 843 of conduit 831 is spaced a vertical distance of H8 from the orifice 850 of conduit 820.

A first purge stream enters through 802 with valve 801 open and enters conduit 830. The location of this first purge is such to insure that conduit 830 becomes completely and uniformly filled with first purge vapor. The first purge vapor exits from orifice 842 of conduit 830 in the form of purge bubbles 840. The vapor from this first purge then enters conduit 831 and exits from orifice 843 of conduit 831 in the form of purge bubbles 841.

A second purge stream enters through conduit 804 with valve 803 open into conduit 820. The vapor from the second purge exits orifice 850 of conduit 820 in the form of purge bubbles 851.

A variety of purge stream rates may be employed for the first and second purges. In practice, the rate at which purge streams enter conduits 830 and 820 are such that small changes, e.g., 10% changes, in the rate at which the purge streams enter these conduits 820 and 830 do not affect the observed pressure differential measured by photocell manometer 18.

Compensation bubbler 816 is added to conduit 830 so as to increase the observed pressure transmitted by conduit 830 to either surface 21 or surface 23 of liquid 24 depending upon whether conduit 830 is a different form of conduit 20 or conduit 30, respectively, of FIG. 1. It is necessary to add additional pressure to that transmitted by conduit 830 to compensate for the difference in pressure impinging on orifice 843 of conduit 831 versus that pressure impinging on orifice 850 of conduit 820.

The operation of the apparatus of FIG. 8 is discussed hereinafter. There are two different types of information that can be obtained from the use of the apparatus disclosed in FIG. 8. The first type of information is an absolute determination of the density of liquid 812. The second type of information is any change in the density of liquid in 812. The error associated with an absolute determination of the density of liquid 812 is considerably greater than the error associated with a determination of the amount of change in the density of liquid 812 over a period of time.

A first purge entering conduits 802 with valve 801 open completely and uniformly fills conduit 830 and conduit 831. The rate at which the first purge enters conduit 830 and exits conduit 831 is such that small, e.g., 10%, changes in the rate of this purge do not change the value of the pressure measured by photocell manometer 18. In a similar way a second purge, preferably using the same vapor as the first purge, enters conduit 804 with valve 803 open and completely and uniformly fills conduit 820. The rate of the second purge is such theat there is no change in pressure measurement of photocell 18 due to small changes, e.g., 10%, in the rate at which the second purge vapor enters conduit 820.

A first reading of millivolt output in determined after the pressures on surfaces 21 and 23 have been equalized by opening valve 861 between conduits 860 and 862. Preferably, the vapor from both the first and second purges are flowing through the apparatus while the first reading of millivolts is being taken.

With valve 861 closed, compensation bubbler 816 is adjusted to provide an additional amount of pressure to compensate for the difference in pressure impinging on orifice 843 of conduit 831 relative to that pressure impinging on orifice 851 of conduit 820. Compensation bubbler 816 is adjusted by adding bubbler liquid 815 to a sufficient height, e.g. L8, above orifice 842 of conduit 830. With bubbler 816 adjusted, photocell manometer is attached to conduits 820 and 830 as shown in FIG. 8 and the differential pressure is measured by means of photocell manometer 18 as discussed in more detail in Example 1. Discussed in more detail in EXAMPLE 4, is the relationship between the density of the liquid, the additional amount of pressure provided by bubbler 816, and the pressure differential between orifices 850 and 843.

The following examples are intended to illustrate the invention of this specification. However, variation thereon would be apparent to one of skill in the art based upon this specification. All such variations are intended to be within the scope of the invention of this specification.

EXAMPLE 1

Beer's Law for scatter of light radiation of frequency f through a liquid of thickness H is: $I_f/I_f^0 = e^{-k_f H}$ where $I_f^0$ is the initial intensity of light radiation of a particular frequency f; $I_f$ is the intensity of light of frequency f transmitted through a layer of liquid of thickness H; and $k_f$ is a physical constant characteristic of the liquid.

For an india ink solution of about 1%, the $k_f$ of Beer's Law for all frequencies of light from a 100 watt bulb are substantially equal. This avoids any problems from using light having different frequencies and different intensities for each such frequency, i.e. Beer's Law simplifies to $I/I^0 = e^{-kH}$.

Any change in the initial intensity, $I^0$, results in a proportional change in the transmitted intensity, I, so that the ratio of $I/I^0$ is unchanged. Consequently, changes in the intensity of light transmitted by a light source due to factors such as changes in line voltage or age of light source, e.g. bulb 34, do not affect the ratio of $I/I^0$ or the H value determined.

Because of the nature of a photoresistor utilizing, for example cadmium sulfide, the internal resistance, R, of the photoresistor is a constant divided by the intensity of light impinging on the photoresistor. Therefore, the ratio $R/R^0$ is equal to the ratio $I^0/I$.

If $V_e/V_d$ is equal to $R/R^0$, then any change due to system variables such as battery voltage changes, temperature changes and mechanical stresses which do not affect the value of H observed also will not affect the ratio of $V_e/V_d$. This is so because $I/I^0$ are only affected by changes in H, provided k remains constant.

Demonstration that:

$V_e/V_d = I^0/I = R/R^0$ for the measuring circuit 40 shown in FIG. 1, wherein

R = internal resistance of detector 38 when a light of intensity I is impinging thereon, $R^0$ = internal resistance of detector 38 when a light of intensity $I^0$ is impinging thereon, $V_e$ = the observed millivolt value recorded on a strip chart when the pressure difference on surfaces 21 relative to surface 23 results in a level difference of H, $V_d$ = the observed millivolt value recorded on a strip chart when the pressures on surfaces 21 and 23 are equal, $V_w$ = voltage across resistor 41 and detector 38, a constant, and $R_c$ = resistance of resistor 41, a constant.

$$(V_e/V_w) = (R/R + R_c) \tag{1}$$

Equations (1) and (2) are derived based on Ohm's Law, i.e.,

V = iR, wherein

V = voltage, i = electrical current, and

R = resistance.

from equation (1)

$$(V_e)(R_c) = R(V_w - V_e) \tag{3}$$

from equation (2)

$$(V_d)(R_c) = R^0(V_w - V_d) \tag{4}$$

dividing equation (3) by equation (4):

$$V_e/V_d = (R/R^0)[(V_w - V_e)/(V_w - V_d)] \tag{5}$$

since $V_w$ is much greater than $V_e$ and $V_d$ $[(V_w - V_e)/(V_w - V_d)]$ is very close to a value of 1, and therefore equation (5) simplifies to:

$$V_e/V_d = R/R^0$$

Also since $I^0/I = R/R^0$ based upon the inherent character of photoresistor 38, therefore, $$V_e/V_d = R/R^0 = I^0/I.$$

Determination of Constant k

A 1% solution of Higgins India Ink in distilled water was used. The constant k for such a solution was found as follows.

$$I/I^0 = e^{-kH} \text{ (Beer's Law for an india ink solution)}$$

$$k = \frac{\ln(I^0/I)}{H}$$

Threaded screw 36 had 20 turns/inch.

The area of measuring cell 28 is 3.73 square centimeters.

The area of the reservoir 22 is 29.9 square centimeters.

d(H) is the change in the height H of the liquid surface 23 due to movement of the measuring cell relative to the reservoir. A movement upward relative to the reservoir will decrease H by d(H), i.e. to a value of H − d(H).

$$d(H) = \left(\frac{29.9}{3.73 + 29.9}\right) \cdot \left(\frac{2.54}{20}\right)(w)$$

w is the number of complete turns of threaded screw 36.

For a given number of turns w, $V^0/V$ is measured. Since $V^0/V = I^0/I$ therefore k is calculated from $$k = \frac{\ln(V^0/V)}{\left(\frac{29.9}{3.73 + 29.9}\right) \cdot \left(\frac{2.54}{20}\right)(w)}$$

$V^0$ = the voltage observed before movement due to w revolutions of the threaded screw.
V = the voltage observed after movement due to w revolutions of the threaded screw.
The value for k was determined to be 94.9 cm$^{-1}$.

Determination of Sensitivity

The smallness of size of d(H) that can be detected by the device of this invention is a measure of the sensitivity of the device.

Since $d(H) = \frac{\ln(V°/V)}{k}$ the sensitivity for a given V° and V by which d(H) can be measured is inversely proportional to the size of k. For example, assume k = 100 cm$^{-1}$, and the change in observed V was 1%, i.e. V° = 101 and V = 100, then the value of d(H) calculated from the above equation is about 10$^{-4}$ centimeters or 1 micron. A 0.1 dyne/square centimeter is equivalent to 1 micron difference in height of water at about 72° F.

EXAMPLE 2

Measurement of Gas Density

In the apparatus of FIG. 3, conduits 320 and 330 are ¼ inch tubing. The distances L1 and L2 are 100 centimeters in length.

An initial value of 95 millivolts is recorded when the pressures on surfaces 21 and 23 of liquid 24 shown in FIG. 1 are equal. The equalization of pressures on surfaces 21 and 23 is achieved by means of conduits 314 and 315 by opening valve 317. Purges, to be discussed, are preferably on, but need not be.

With valve 317 closed, a reference purge is introduced at a rate of 5 millivolts (mls) per minute. The reference purge consists of atmospheric air having a density of approximately 1.2×10$^{-3}$ grams (gm)/ml. A sample purge of vapor is introduced at about the same rate through conduit 311. Purge rates for the sample purge or the reference purge must be large enough to completely and uniformly fill the tubing corresponding to lengths L1 and L2; but small enough so as not to cause any detectable pressure changes due to the flow of purge vapors. In practice, a fluid-head value which is not affected by small changes in purge rates is indicative of a valid and reproduceable result. A value of 94 millivolts is recorded.

A total of 1500 millivolts are applied across resistor 41 and detector 38 shown in FIG. 1.

The ratio resistances $R/R_0$ is calculated as follows:

$$R/R_0 = \frac{94(1500 - 95)}{95(1500 - 94)} = 0.9888$$

The 1% India ink solution used had a light absorption coefficient k corresponding to the k in Beer's Law of about 100 reciprocal centimeters.

The pressure differential is then calculated from the following equation:

$$\text{Del.}(P) = 1.1248 \ De \ \ln(R/R_0)/k$$

where Del.(P) is gm/cm$^2$ and De is ink density in grams per cubic centimeter, i.e., 1 gm/cm$^3$. The pressure change found is −0.000127 gm/cm$^2$. The vapor in conduit 320 has a density relative to the vapor in conduit 330 of 0.000127/100 grams per cubic centimeter less than the density of the vapor in conduit 330.

From this example, it is clear that the device disclosed can detect a change in vapor density equal to about 0.1% of the density of atmospheric air, and can continuously record this and subsequent changes.

EXAMPLE 3

Measurement of a Gasoline Leak

In FIG. 5, conduit 520 of ¼ inch tubing has its orifice 551 near the bottom of gasoline tank 550. Conduit 530 has its orifice below the surface of a mercury column contained in reference bubbler 513. Both conduit 520 and 530 are separately purged with air at a rate of about 5 mls per minutes. The rates and pressure of these purges are adjusted to keep the line free from liquid either entering orifice 551 of conduit 520 from tank 500 or entering orifice 550 of conduit 530 from bubbler 513. However, the rate is such that there are no pressure changes due to the flow of any purge vapor. The depth L4 of the mercury in reference bubbler 513 is adjusted to approximately balance the pressure due to gasoline present in tank 500 prior to hooking up the photocell manometer 18 as shown in FIG. 5.

After connecting the manometer as shown in FIG. 5, the ink level is adjusted by means of the adjusting screw 36 so that the signal recorded on chart 55 of millivolt recorder 42 is near the top of the chart recorder. The initial signal is found to be 95 millivolts out of a total of 1500 millivolts which is applied across resistor 41 and detector 38 as shown in FIG. 1. Over night the signal drops to 94 millivolts.

The ratio of resistance is calculated as follows:

$$R/R_0 = \frac{94(1500 - 95)}{95(1500 - 94)} = 0.9888$$

The pressure change is calculated as follows: Del.(P) = 1.1248 De ln(R/R$_0$)/k where De is equal to 1 gm/cm$^3$.

Liquid surface in the tank is 6 feet by 10 feet or 55,742 cm$^2$. The loss of mass is 55,742×0.000127 or 7.08 grams. 7.08 grams corresponds to about 9 ml of gasoline or about 1/100 of a quart.

EXAMPLE 4

Measurement of Liquid Density

Prior to attaching photocell manometer 18 as shown in FIG. 8, the pressure transmitted by conduit 820 and the pressure transmitted by conduit 830 to surfaces 21 and 23, respectively, are approximately balanced by means of compensation bubbler 816. The compensation procedure involves adding mercury as bubbler liquid 815. In this example, L8 is 24 centimeters of mercury which provides a constant pressure of 324.99 gm/cm$^2$ at 72° F. The preferred rate for the first and second purge is approximately 5 ml per minute. Conduits 820, 830, and 831 are ¼ inch tubing. Small changes, e.g., about 10%, in the flow rate of purge streams entering through conduits 803 and 804 do not change the millivolt value recorded on chart 55.

A first reading on the photocell manometer 18 with valve 861 open and the pressures on surfaces 21 amd 23 substantially the same is found to be 10 millivolts. The value of k for the 1% India ink soution is 100 reciprocal centimeters. With the above conditions maintained, but with valve 861 closed two readings were taken, one at the end of the first hour is 95 millivolts, and the other at the end of 4 hours is 96 millivolts. The total voltage applied across resistor 41 and detector 38 of FIG. 1 is 1500 millivolts.

The ratio of resistances is calculated as follows:

$$R/R_0 = \frac{95(1500 - 10)}{10(1500 - 95)} = 10.0747$$

The pressure differential measured by photocell manometer 18 for the pressure on surfaces 21 and 23 is calculated as follows:

Del.$(P) = 1.1248 \, De \, \ln(R/R_0)/k = 0.0620 \, gm/cm^2$

Absolute density of liquid 812 is determined as follows:

$PL = $ Del.$(P) + Pm$ where $PL = $ pressure difference of the liquid 812 at orifice 850 as compared to orifice 843.

Del.$(P) = $ differential pressure measured by photocell manometer 18.

$Pm = $ the pressure due to mercury in compensation bubbler 816.

$PL = 0.0260 \, gm/cm^2 + 324.99 \, gm/cm^2$ $PL = 325.02 \, gm/cm^2$

Since H8 is 304.8 cm and
D(Density of liquid) = (PL/H8)
$D = 325.02/304.8$
$D = 1.0663 \, gm/cm^3$ The change in density over time measured by a change in millivolts of 95 to 96 is calculated as follows:

$$R/R_0 = \frac{96(1500 - 95)}{95(1500 - 96)} = 1.0112$$

Del.$(P) = 1.1248 \, De \, \ln(1.0112/100)$
$= 0.0001258 \, gm/cm$

Change in Density $= \frac{Del.(P)}{H8}$
$= 0.0001258/304.8$
$= 4.127 \times 10^{-7} \, gm/cm^3$ It is clear that the pressure of the absolute density measurement is limited by the accuracy of the measurement relating to the compensation bubbler 816, i.e., about plus or minus 0.001 $gm/cm^3$. However, relative measurements to determine changes in density of liquid 812 wherein the component of pressure from compensation bubbler 816 merely acts as a constant which does not change the value determined, the determination of the density change of liquid 812 can be made to plus or minus $2 \times 10^{-7} \, gm/cm^3$.

EXAMPLE 5

Measuring the Change in Level of an Oil/Water Interface

A photocell manometer 18 is connected as shown in FIG. 6. The orifice 650 of conduit 620 is in the oil phase. The orifice 651 of conduit 630 is in the water phase. Orifice 650 is separated by a fixed vertical distance of H2 from orifice 651. Any change in the pressure differential measured by photocell manometer 18 indicates a change in the location of interface 603.

The following derived equation gives the relationship between a change in the differential pressure measured by photocell manometer 18 and a change in location of interface 603, i.e., (H1−H1′).

$$P_0 = D_w(H2 - H1) + D_0 H1$$
$$P = D_w(H2 - H1') + D_0 H1'$$
$$(P - P_0) = D_w(H1 - H1') + D_0(H1' - H1)$$
$$= (D_w - D_0)(H1 - H1')$$

$P_0$ is the differential pressure measured as in Example 4 by photocell manometer 18 with interface 603 located initially at a vertical distance of H1 and later at a vertical distance of H1′ from orifice 650 of conduit 620. P is the differential pressure measured by photocell manometer 18 when interface 603 is located at some distance H1′ from orifice 630. $D_w$ is the density of the water phase. $D_0$ is the density of the oil phase.

Using the above equation, a pressure change of 0.000127 $gm/cm_2$ is measured and recorded. The density of water is 1 gm/ml and the density of oil 0.8 gm/ml. The change in level H1−H1′ is 0.000635 centimeters or 6.35 microns.

Measuring the interface in this way can also be useful as a means for measuring leaks because oil-water interfaces of the kind described can sometimes be found at the bottom of storage tanks.

EXAMPLE 6

Measuring a Change in the Concentration of Entrained Solids or Droplets

Orifices 450 and 451 of conduits 430 and 420, respectively, are spaced 60 centimeters apart in a distillation column 417. Conduits 420 and 430 are purged as described hereinabove in the other application.

A first pressure differential pressure is made wherein the pressure on surfaces 21 and 23 of liquid 24 of FIG. 1 are equal. A second pressure determination is made with the apparatus operating as shown in FIG. 4. A differential pressure change of 0.000127 gm/cm squared is observed.

A change of 0.000127 corresponds to a density change of $1.32 \times 10^{-4}$ lbs per cubic foot. Solids entrained in a gas is a perameter of considerable importance in fluid cracking units. The concentration of entrained solids entering the cyclones, for example, can vary from 0.05 lbs per cubic foot to 0.8 lbs per cubic foot. Since the photocell can detect changes of less than 1% and perhaps even lower, the range of such entrained solids can be readily measured.

Entrainment of liquid droplets in a distillation tower can have substantial impact upon the efficiency of such a tower. Entrained liquid, for example, can travel from distillation tray to distillation tray without complete evaporation and condensation. The efficiency and equilibrium stability of the distillation tower is impacted.

The photocell manometer can measure the contribution of such entrained liquid droplets in the vapor during distillation.

The embodiments of this invention in which an exclusive property or privilege is claimed are defined as follows:

1. A process for measuring changes in the amount of solids or liquids entrained in a vapor contained in a container by means of a photocell manometer having an orifice of a first sensor and an orifice of a second sensor located at different levels in vapor contact with said vapor within said container, said process comprising:

introducing a first vapor purge stream into said first sensor at a rate at least sufficient to maintain said first sensor uniformly filled with a vapor from said first vapor purge stream, introducing a second vapor purge stream into said second sensor at a rate at least sufficient to maintain said second sensor uniformly filled with a vapor from said second vapor purge stream, locating said orifice of said first sensor at a different relative height to said orifice of said second sensor, and measuring a relative pressure transmitted by said first sensor relative to a pressure transmitted by said second sensor, whereby changes in said relative pressure indicate changes in said amount of entrained solids or liquids.

* * * * *

UNITED STATES PATENT AND TRADEMARK OFFICE
CERTIFICATE OF CORRECTION

PATENT NO.   : 4,420,966
DATED        : December 20, 1983
INVENTOR(S)  : Lloyd A. Baillie, et al.

It is certified that error appears in the above–identified patent and that said Letters Patent are hereby corrected as shown below:

Column 4, line 54, delete "antoher" and insert in place thereof -- another --.

Column 10, line 33, delete "413" and insert in place thereof -- 513 --.

Column 14, line 61, delete "theat" and insert in place thereof -- that --.

Column 14, line 65, delete "in" and insert in place thereof -- is --.

Column 16, line 8, delete "(Ve/Vw)=(R/R+Ro)   (1)" and insert in place thereof --
(Ve/Vw)=(R/R+Rc)    (1) --.

Column 16, after line 8, add -- (Vd/Vw)=(R°/R°+Rc)   (2) --.

Column 17, line 42, delete "millivolts" and insert in place thereof -- milliliters --.

Column 18, line 17, delete "550" and insert in place thereof -- 500 --.

Signed and Sealed this

Twenty-ninth Day of January 1985

[SEAL]

Attest:

DONALD J. QUIGG

Attesting Officer    Acting Commissioner of Patents and Trademarks